United States Patent
Bristol

(10) Patent No.: US 8,596,108 B2
(45) Date of Patent: Dec. 3, 2013

(54) GAS MEASURING DEVICE AND METHOD OF OPERATING THE SAME

(75) Inventor: L. Rodney Bristol, Chalfont, PA (US)

(73) Assignee: Scott Technologies, Inc., Boca Raton, FL (US)

( * ) Notice: Subject to any disclaimer, the term of this patent is extended or adjusted under 35 U.S.C. 154(b) by 1159 days.

(21) Appl. No.: 12/238,889

(22) Filed: Sep. 26, 2008

(65) Prior Publication Data

US 2009/0084158 A1    Apr. 2, 2009

Related U.S. Application Data

(60) Provisional application No. 60/997,084, filed on Oct. 1, 2007.

(51) Int. Cl.
    *G01N 7/00*    (2006.01)
(52) U.S. Cl.
    USPC ........................................ 73/25.01
(58) Field of Classification Search
    USPC ......... 73/31.05, 31.06, 23.2, 25.03; 29/592.1, 29/593; 204/424
    See application file for complete search history.

(56) References Cited

U.S. PATENT DOCUMENTS

| | | |
|---|---|---|
| 3,946,198 A | 3/1976 | Foote |
| 4,464,244 A | 8/1984 | Uchida et al. |
| 4,504,732 A | 3/1985 | Bube et al. |
| 4,509,034 A | 4/1985 | Sakai |
| 4,524,264 A | 6/1985 | Takeuchi et al. |
| 4,541,988 A | 9/1985 | Tozier et al. |
| 4,627,269 A | 12/1986 | Forster et al. |
| 4,823,803 A | 4/1989 | Nakamura |
| 4,847,783 A | 7/1989 | Grace et al. |
| 4,911,892 A | 3/1990 | Grace et al. |
| 4,916,935 A | 4/1990 | Novack et al. |
| 5,656,827 A | 8/1997 | Kang et al. |
| 6,044,689 A | 4/2000 | Yoshida et al. |

(Continued)

FOREIGN PATENT DOCUMENTS

| | | |
|---|---|---|
| EP | 0743516 | 11/1996 |
| EP | 0878707 A1 | 4/1998 |

(Continued)

OTHER PUBLICATIONS

PCT ISR and Written Opinion; PCT/US2008/011380; F-TP-00290WO; Scott Technologies, Inc.; dated Apr. 17, 2009; 13 pages.

*Primary Examiner* — Peter Macchiarolo
*Assistant Examiner* — Tamiko Bellamy
(74) *Attorney, Agent, or Firm* — Wyatt B. Pratt

(57) ABSTRACT

A gas measuring device for measuring a presence of a target gas in a fluid medium includes a sensor having a sensing element and a heating element being configured to heat the sensing element to a predetermined operating temperature. The sensing element is responsive to the target gas such that at least one electrical property of the sensing element varies based on a presence of the target gas, and the electrical property of the sensing element is measured by the gas measuring device. The gas measuring device also includes a control circuit having a heating element controller connected to, and measuring an electrical property of, the heating element. The control circuit also includes a heater power supply supplying power to the heating element, wherein the heating element controller is connected to, and controls the operation of, the heater power supply based on the measurement of the electrical property of the heating element.

19 Claims, 3 Drawing Sheets

(56) References Cited

U.S. PATENT DOCUMENTS

| | | | |
|---|---|---|---|
| 6,055,849 A | 5/2000 | Shioiri et al. | |
| 6,173,602 B1 | 1/2001 | Moseley | |
| 6,294,075 B1 | 9/2001 | Poggio et al. | |
| 6,540,892 B1 | 4/2003 | Strohmaier | |
| 6,580,280 B2 | 6/2003 | Nakae et al. | |
| 6,586,711 B2 | 7/2003 | Whitney et al. | |
| 6,596,236 B2 | 7/2003 | DiMeo, Jr. et al. | |
| 6,613,207 B1 | 9/2003 | De La Prieta et al. | |
| 6,742,382 B2 | 6/2004 | Warburton et al. | |
| 6,812,708 B2 | 11/2004 | Bristol | |
| 6,833,535 B2 * | 12/2004 | Streit et al. | 219/492 |
| 6,870,142 B2 | 3/2005 | Hada et al. | |
| 6,921,883 B2 | 7/2005 | Kato et al. | |
| 7,084,379 B2 * | 8/2006 | Saito et al. | 219/497 |
| 7,185,528 B2 | 3/2007 | Bristol | |
| 7,193,187 B2 | 3/2007 | Chen et al. | |
| 7,385,161 B2 | 6/2008 | Smith | |
| 7,655,887 B2 * | 2/2010 | Chen et al. | 219/505 |
| 2002/0000436 A1 | 1/2002 | Hashimoto et al. | |
| 2003/0178016 A1 * | 9/2003 | Nebiyeloul-Kifle et al. | 123/676 |
| 2005/0103772 A1 | 5/2005 | Streit et al. | |
| 2006/0068080 A1 | 3/2006 | Yadav et al. | |
| 2006/0117737 A1 | 6/2006 | Ohsaki | |
| 2007/0012565 A1 | 1/2007 | Suzuki et al. | |
| 2007/0102294 A1 | 5/2007 | Dorisio Deininger et al. | |
| 2007/0116606 A1 | 5/2007 | Kiesewetter et al. | |
| 2007/0202012 A1 | 8/2007 | Steichen et al. | |
| 2007/0206654 A1 | 9/2007 | Merziliakov | |

FOREIGN PATENT DOCUMENTS

| | | |
|---|---|---|
| JP | 08313476 A * | 11/1996 |
| JP | 2003172719 A * | 6/2003 |
| RU | 2171468 C1 | 7/2001 |
| RU | 2304278 C1 | 8/2007 |
| WO | WO 95/00836 | 1/1995 |

* cited by examiner

GAS MEASURING DEVICE AND METHOD OF OPERATING THE SAME

This application claims priority to and the benefit of the filing date of U.S. Provisional Application No. 60/997,084 filed Oct. 1, 2007 for "GAS MEASURING DEVICE AND METHOD OF OPERATING THE SAME," which is hereby incorporated by reference in its entirety.

BACKGROUND OF THE INVENTION

The subject matter herein relates generally to gas measuring devices and methods of operating gas measuring devices.

Gas measuring devices having sensors that detect certain chemicals or gases in air are utilized in many applications. For example, the detection of noxious gases such as carbon monoxide, hydrogen sulfide, nitrogen oxides, and the like is desirable so that a signal can be generated indicating the presence of such gases. Appropriate steps can then be taken to mitigate their effect or to remove persons from the presence of the gases.

One type of gas measuring device used to detect gas presence is a metal oxide semiconductor to provide early warning of the development of an explosion hazard (e.g. escaping flammable gas) or the presence of toxic gases or vapors in ambient air. The device typically includes a sensor provided on a heated substrate and that includes two metallic electrodes connected to the sensor. The presence of gas posing a hazard is detected by a sensible change in the resistance of the sensor by means of the electrodes that are incorporated in a suitable electric circuit.

The reactions that allow the detection of target gases normally involve the oxidation of the target gas at the semiconductor (oxide) surface and a change in the electrical properties of the material. However, conventional sensors may be impacted by changes in temperature or humidity. Maintaining a constant temperature of the sensing element has proven problematic. At least some known devices have overcome such problems by superheating the sensor and maintaining the sensor at a superheated temperature, such that the sensor is less effected by changes in temperature. However, maintaining the sensor at superheated temperatures requires more power to operate the device.

A need remains for a gas measuring device and sensor that may be manufactured and operated in a cost effective and reliable manner.

BRIEF DESCRIPTION OF THE INVENTION

In one embodiment, a gas measuring device is provided for measuring a presence of a target gas in a fluid medium, wherein the gas measuring device includes a sensor having a sensing element and a heating element being configured to heat the sensing element to a predetermined operating temperature. The sensing element is responsive to the target gas such that at least one electrical property of the sensing element varies based on a presence of the target gas, and the electrical property of the sensing element is measured by the gas measuring device. The gas measuring device also includes a control circuit having a heating element controller connected to, and measuring an electrical property of, the heating element. The control circuit also includes a heater power supply supplying power to the heating element, wherein the heating element controller is connected to, and controls the operation of, the heater power supply based on the measurement of the electrical property of the heating element.

Optionally, the heating element may be controlled to maintain a substantially constant temperature of the sensing element. The heating element controller may measure a resistance of the heating element, and the heating element controller may control the operation of the heater power supply based on the measured resistance of the heating element. Optionally, the sensor may include a substrate having the sensing element applied to one side of the substrate and the heating element applied to the opposite side of the substrate, wherein the substrate thermally conducts heat from the heating element to the sensing element. The control circuit may also include a sensing element controller connected to, and measuring the at least one electrical property of, the sensing element, wherein the sensing element controller is one of integrally formed with, and separately provided from, the heating element controller.

In another embodiment, a gas measuring device is provided for measuring a presence of a target gas in a fluid medium, wherein the gas measuring device includes a sensor having a sensing element and a heating element being configured to heat the sensing element to a predetermined operating temperature. The sensing element is responsive to the target gas such that at least one electrical property of the sensing element varies based on a presence of the target gas. The gas measuring device also includes a sensing circuit having a sensing power supply for supplying power to the sensing element and a sensing element controller measuring the at least one electrical property of the sensing element. The gas measuring device further includes a heating circuit having a heater power supply supplying power to the heating element and a heating element controller connected to, and measuring at least one electrical property of, the heating element. The heating element controller controls the operation of the heater power supply using pulsed modulation based on the measurement of the electrical property of the heating element.

In a further embodiment, a method of manufacturing a gas measuring device is provided that includes providing a sensor having a sensing element and a heating element being configured to heat the sensing element to a predetermined operating temperature, wherein the sensing element is responsive to a target gas such that at least one electrical property of the sensing element varies based on a presence of the target gas. The method also includes connecting a sensing control circuit to the sensing element, wherein the sensing control circuit supplies power to the sensing element and measures changes in the at least one electrical property of the sensing element relating to the presence of the target gas. The method further includes connecting a heating control circuit to the heating element, wherein the heating control circuit supplies power to the heating element according to a pulse modulated control scheme and measures at least one electrical property of the heating element. The pulse modulated control scheme varies based on the measured electrical property.

In yet another embodiment, a method of operating a gas measuring device is provided that includes providing a sensor having a sensing element and a heating element being configured to heat the sensing element to a predetermined operating temperature. The method also includes supplying power to the heating element, utilizing pulse modulation to control power to the heating element, determining a resistance of the heating element, utilizing changes in the resistance of the heating element to change the pulse modulation to maintain the heating element at a constant temperature, and measuring a resistance of the sensing element. The sensing element is responsive to a target gas such that the resistance of the sensing element varies based on a presence of the target gas.

DETAILED DESCRIPTION OF THE INVENTION

Figure 1:
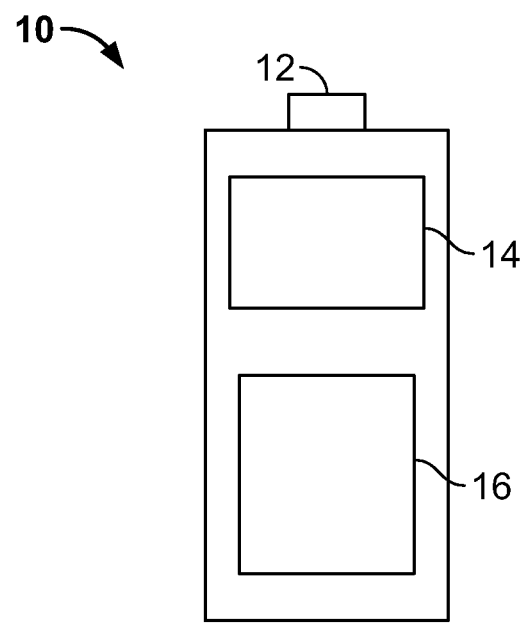
FIG. 1 illustrates a gas measuring device having a sensor formed in accordance with an exemplary embodiment.

FIG. 1 illustrates a gas measuring device 10 having a sensor 12. The gas measuring device 10 is used for measuring a presence of a certain gas or gases in a fluid medium, such as air. The gas measuring device 10 may be used for measuring the presence of noxious, toxic, combustible or other harmful type of gas that may be present in the fluid medium. For example, the gas measuring device 10 may be used to detect for gases such as hydrogen sulfide, carbon monoxide, nitrogen oxides, and the like. In one embodiment, the gas measuring device 10 merely detects whether or not the gas is present. In other embodiments, the gas measuring device 10 may detect the amount or concentration of the gas when present.

The gas measuring device 10 communicates results, such as the concentration of the gas, by any known method, such as on a display 14. Optionally, a user interface 16, such as a keypad, may be provided for user interaction with the device 10. Optionally, the gas measuring device 10 may alert the user as to the presence of a gas, or the presence of a gas above a threshold level, such as with an audible or visible alarm. In some embodiments, the gas measuring device 10 may communicate with other devices or systems to alert the device or system as to the presence of a gas. Such communication may be wired or wireless. The gas measuring device 10 may be portable and carried by a user, or alternatively, may be mounted to a structure in a desired location.

The sensor 12 is provided on the gas measuring device 10 such that the sensor 12 is exposed to the air surrounding the gas measuring device 10. While the sensor 12 is illustrated as being provided on an external surface of the gas measuring device 10, the sensor 12 may be internally housed within the gas measuring device 10 and air flow may be directed to the sensor 12, such as through a port open to the external environment or by air being pumped to the sensor 12. The sensor 12 may be similar to the sensor illustrated and described in copending U.S. patent application titled "GAS MEASURING DEVICE AND METHOD OF MANUFACTURING THE SAME" filed concurrently and incorporated by reference herein.

Figure 2:
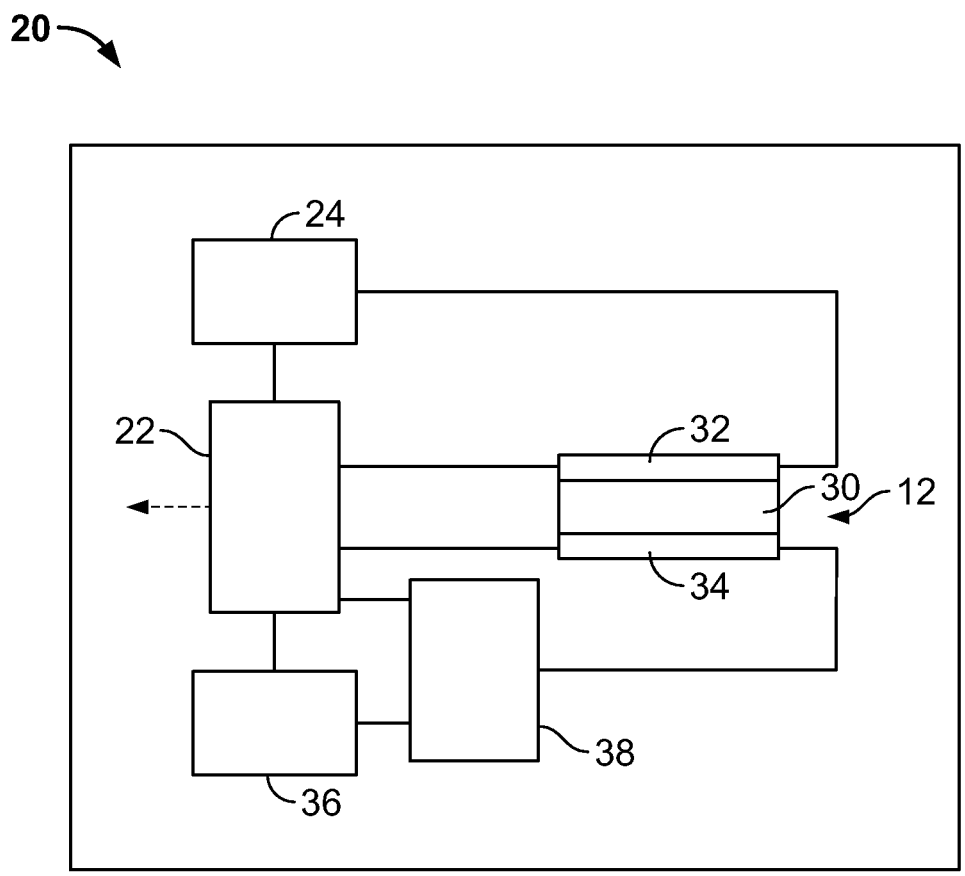
FIG. 2 illustrates a control circuit for the gas measuring device and sensor shown in FIG. 1.

FIG. 2 schematically illustrates a control circuit 20 for the gas measuring device 10 and sensor 12. The control circuit 20 includes a controller 22 that is operatively connected to the sensor 12. The control circuit 20 also includes a low voltage power supply 24 that is operatively connected to the sensor 12.

In an exemplary embodiment, the sensor 12 is a metal oxide sensor, however, other types of sensors may be used with the gas measuring device 10, and the metal oxide sensor illustrated in the figures is illustrative and is not intended to be limiting. The sensor 12 includes a substrate 30, such as a ceramic insulator. One example of a substrate 30 for the sensor 12 is an alumina substrate. The sensor 12 also includes a sensing element 32 on the substrate 30 and a heating element 34 on the substrate 30. In an exemplary embodiment, the sensing element 32 includes a gas sensitive material and is applied to one side of the substrate 30. The heating element 34 is applied to the opposite side of the substrate 30. In an alternative embodiment, the sensing element 32 and the heating element 34 may be applied to the same side of the substrate 30. Optionally, the sensor 12 may be layered structure, wherein the sensing element 32 and/or the heating element 34 are layers applied to the substrate 30. For example, the sensing element 32 may be a film material screen printed on the substrate 30. The sensing element 32 may be a porous nanostructure. Similarly, the heating element 34 may be a film material screen printed on the substrate 30. The heating element 34 may be a ceramic micromachined heater.

The low voltage power supply 24 is operatively connected to the sensing element 32 and supplies a predetermined voltage to the sensing element 32. Optionally, the voltage supplied may be a constant voltage. The controller 22 is also connected to the sensing element 32 and measures at least one electrical property of the sensing element 32, such as a resistance, a conductance, a capacitance, and/or an impedance. The sensing element 32 is manufactured using a material having electrical properties that are affected by the presence of a predetermined target gas. For example, the sensing element 32 may be responsive to the gas such that the electrical properties of the sensing element 32 vary based on the presence and/or concentration of the gas. In an exemplary embodiment, gas adsorption on the surface of the sensing element 32 causes a change in electrical properties of the sensing element 32, such as a change in resistance. The changes in the electrical properties are detected and/or measured by the controller 22.

In an exemplary embodiment, the gas reactions with the sensing element 32 occur when the sensing element 32 is at an elevated temperature. The heating element 34 is used to elevate the temperature of the sensing element 32 to a predetermined temperature. A heater power supply 36 is provided for supplying power to the heating element 34. The amount of power supplied, the duration of the pulses and the frequency of the pulses affect the temperature of the heating element 34, and thus the sensing element 32. For example, in operation, when the heating element 34 is powered, the temperature of the substrate 30 is elevated, which thus raises the temperature of the sensing element 32 to a predetermined level. When the temperature of the sensing element 32 is at a predetermined level, the sensing element 32 may react with the gas at the surface of the sensing element 32. Additionally, because the electrical properties may be affected by the temperature of the sensing element 32, maintaining a constant temperature of the sensing element 32 may provide more accurate results.

The power supply 36 is operatively controlled by the controller 22. For example, the controller 22 may control the amount of power supplied, the duration of the power supply and the frequency of the power supply. In one embodiment, a pulse modulation driver 38 is provided within the control circuit 20. The controller 22 is coupled to the driver 38 and operates to control the amount of power supplied, the duration of the power supply and/or the frequency of the power supply according to a pulse modulation control scheme. Pulsing the power supply to the heating element 34 may reduce the overall power consumption of the gas measuring device 10 as compared to continuously powered operating schemes.

In alternative embodiments, other control schemes other than pulse modulation may be implemented to control the power supply to the heating element 34. For example, the heater power supply voltage may be proportionally controlled to maintain a desired heater resistance, where heater resistance is calculated from the ratio of heater voltage and a measurement of heater current.

In an exemplary embodiment, the controller 22 is also connected to the heating element 34 to measure an electrical property of the heating element 34, such as a resistance, a conductance, a capacitance, and/or an impedance. Because the electrical properties of the heating element 34 may be related to the temperature of the heating element 34, the temperature of the heating element 34 may be controlled by measuring at least one electrical property and maintaining the electrical property at a substantially constant level. For example, the resistance of the heating element 34 may be directly proportional to the temperature of the heating element. Maintaining the heating element 34 at a substantially constant resistance may thus maintain the heating element 34 at a constant temperature. The heating element 34 may be maintained at a constant resistance by controlling the pulse modulation control scheme. As such, the temperature of the heating element 34 may be calculated and/or changed based on a measured electrical property of the heating element 34, such as the resistance.

In operation, when the controller 22 detects the presence of the gas, the controller 22 may output a signal relating to such presence and/or the concentration of the gas. The signal output from the controller 22 may be used by the gas measuring device 10 to alert the user and/or to display information relating to the presence/concentration of gas. In an exemplary embodiment, the controller 22 may include circuitry or circuit components, such as an amplifier that manipulates the signal from the sensing element 32, and/or an analog-to-digital converter that manipulates the signal from the sensing element 32. The manipulated signal may be output from the controller 22, or otherwise used by the gas measuring device 10 to perform other functions of the gas measuring device 10, such as the alerting or displaying. While the controller 22 is illustrated as being a common controller 22 that is operatively connected to both the heating element 34 and the sensing element 32, the control circuit 20 may include more than one controller.

Figure 3:
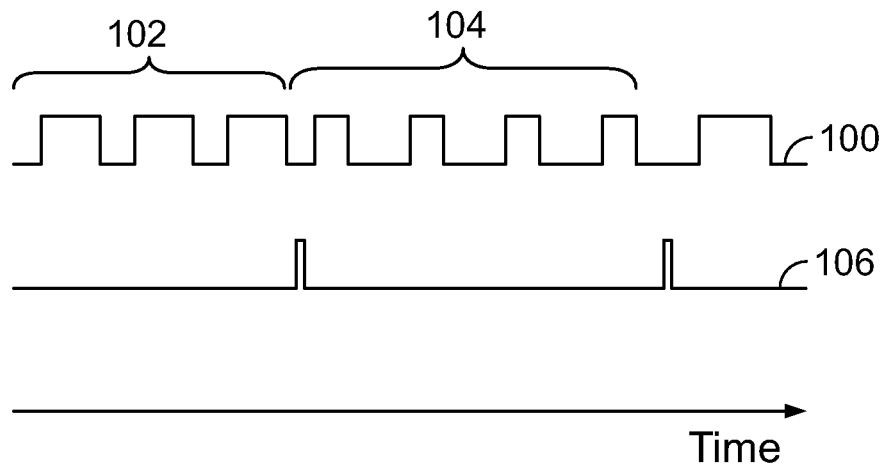
FIG. 3 is a graph including waveforms illustrating an exemplary operation of the control circuit shown in FIG. 2.

FIG. 3 is a graph including waveforms illustrating an exemplary operation of the control circuit 20 (shown in FIG. 2). The waveform 100 represents the voltage appearing on an input electrode connected to the heating element 34 (shown in FIG. 2). The controller 22 and/or the pulse modulation driver 38 control the amount of voltage supplied, the duration that the voltage is supply and/or the frequency that the voltage is supplied. By changing the pulses, the amount of power supplied to the heating element is likewise changed, which will increase or decrease the temperature of the heating element 34, and thus the temperature of the sensing element 32. For example, FIG. 3 illustrates a first set of pulses 102 having a certain duration and a second set of pulses 104 having a different, shorter duration. The frequency and amount of voltage are the same for the first and second sets of pulses 102, 104, however, the frequency or amount could also be changed to change the power supply to the heating element 34. Additionally, the shape of the pulse may be changed or may be different than the rectangular pulses illustrated in FIG. 3 in alternative embodiments.

The waveform 106 represents the controller measurement of the electrical properties of the heating element 34. The measurement of the electrical property is taken during an "off" time (e.g. when the heating element 34 is not being powered). In an exemplary embodiment, the resistance of the heating element 34 is measured by the controller 22, however, as described above, other electrical properties may be measured in addition to or in lieu of the resistance. Optionally, and as illustrated in FIG. 3, the measurements may be taken after a given number of pulses, however, the measurement may be taken after each pulse in alternative embodiments.

Figure 4:
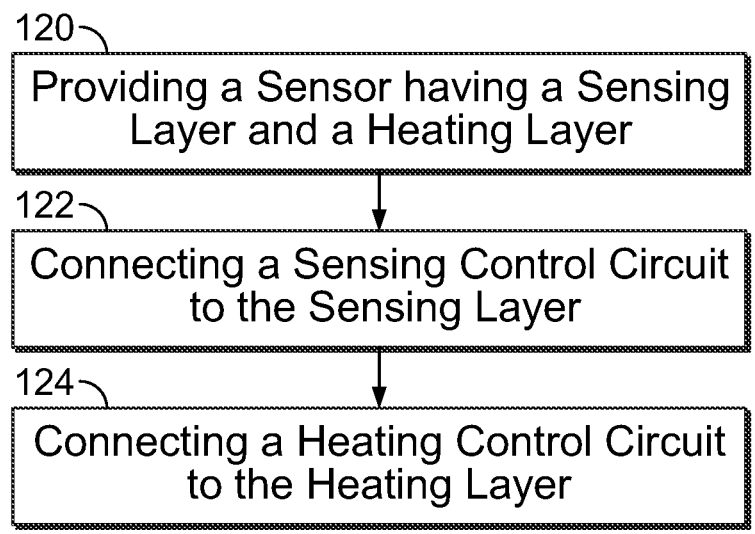
FIG. 4 is a flow chart for an exemplary method of manufacturing a gas measuring device, such as the gas measuring device shown in FIG. 1.

FIG. 4 is a flow chart illustrating an exemplary method of manufacturing a gas measuring device, such as the gas measuring device 10 (shown in FIG. 1). The method includes providing 120 a sensor having a sensing element and a heating element being configured to heat the sensing element to a predetermined operating temperature. The sensing element is responsive to a predetermined target gas such that at least one electrical property of the sensing element varies based on a presence of the predetermined target gas.

The method also includes connecting 122 a sensing control circuit to the sensing element. The sensing control circuit supplies power to the sensing element. The power supply may be constant or varied. The sensing control circuit measures changes in the electrical properties of the sensing element relating to the presence of the predetermined target gas. In an exemplary embodiment, the sensing control circuit measures changes in a resistance of the sensing element, wherein the resistance is affected by the presence of the gas. The resistance may also be affected by the temperature of the sensing element. As such, the sensing element may be maintained at a substantially constant temperature during operation. Additionally, once the electrical property value is measured, the sensing control circuit may send a signal to another system or component within the gas measuring device to either display the result of the presence and/or concentration of the gas. The sensing control circuit may also send a signal relating to an alert to alert the user as to the presence or concentration of the gas.

The method further includes connecting 124 a heating control circuit to the heating element. The heating control circuit supplies power to the heating element according to a pulse modulated control scheme and measures at least one electrical property of the heating element. The pulse modulated control scheme may be varied or controlled based on the measured electrical property. Optionally, the pulse modulated control circuit may vary the power supply to maintain the measured electrical property at a constant value. In one embodiment, a pulse modulating driver may be provided for controlling at least one of the amount, duration and/or frequency of pulses to the heating element. The heating control circuit may be connected to measure an electrical property that varies based on temperature and the heating control circuit may maintain a substantially constant temperature of the heating element by maintaining the measured electrical property at a substantially constant value by varying the pulse modulated control scheme. For example, the measured electrical property may be the resistance of the heating element, which varies based on the temperature of the heating element. Because the resistance is directly proportional to the temperature, the resistance is maintained at a substantially constant value to maintain a substantially constant temperature. As such, when the resistance is above or below the desired operating resistance, the controller may change the pulse modulated control scheme to bring the resistance value to the desired operating resistance.

Figure 5:
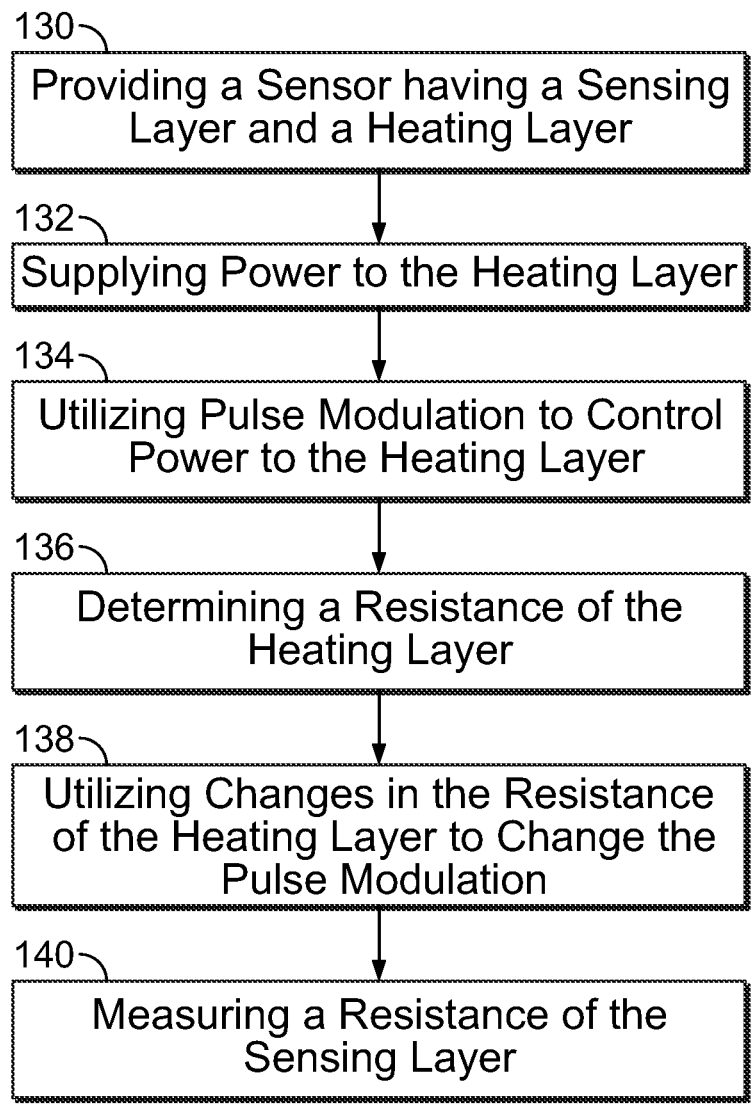
FIG. 5 is a flow chart for another exemplary method of manufacturing a gas measuring device, such as the gas measuring device shown in FIG. 1.

FIG. 5 is a flow chart illustrating another exemplary method of operating a gas measuring device, such as the gas measuring device 10 (shown in FIG. 1). The method includes providing 130 a sensor having a sensing element and a heating element being configured to heat the sensing element to a predetermined operating temperature. The sensing element and heating element may be provided on opposite sides of a substrate, or may be directly applied to one another. The footprints (e.g. the sizes and shapes) of the layers may be substantially similar and the layers may be substantially aligned with one another. The sensing element is in thermal communication with the heating element such that the heating element may heat the sensing element.

The method includes supplying 132 power to the heating element. The power may be supplied according to a control scheme. In an exemplary embodiment, the method includes utilizing 134 pulse modulation to control power to the heating element. The pulse modulation power scheme may be controlled by a controller and/or a pulse modulation driver that operates as a gate between the power supply and the heating element.

The method includes determining 136 a resistance of the heating element. The resistance is determined as a measure of the temperature of the heating element. In one embodiment, a controller is connected to the heating element and measures electrical properties, such as the resistance, of the heating element. The measured resistance may be compared to a desired operating resistance. The method includes utilizing 138 changes in the resistance of the heating element to change the pulse modulation to maintain the heating element at a constant temperature. For example, when the resistance is raised or lowered, the controller determines that the temperature is raised or lowered. Optionally, a measured resistance corresponds to a certain temperature, and a constant value for the resistance correspond to a constant temperature. Thus, any change in the resistance may necessitate a change in the power supplied to the heating element to correct for the change in temperature.

The method includes measuring 140 a resistance of the sensing element. Because the sensing element is responsive to a predetermined target gas, changes in the resistance of the sensing element may be based on a presence of the predetermined target gas. The gas measuring device is operated by measuring a resistance value, which corresponds to a presence and/or certain concentration of the gas. Additionally, because the resistance is affected by the temperature of the sensing element, the heating element is controlled by the pulse modulation control scheme to maintain a substantially constant temperature of the sensing element. When the temperature is constant, changes in the resistance are attributable to presence of the gas. Additionally, the gas measuring device may be calibrated to correlate the resistance of the sensing element with the presence and/or concentration of the gas. For example, the gas measuring device may be calibrated according to the method described in copending U.S. patent application titled "GAS MEASURING DEVICE AND METHOD OF MANUFACTURING THE SAME"

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A gas measuring device for measuring a presence of a target gas in a fluid medium, the gas measuring device comprising:
   a sensor having a sensing element and a heating element being configured to heat the sensing element to a predetermined operating temperature, the sensing element being responsive to the target gas such that at least one electrical property of the sensing element varies based on a presence of the target gas, wherein the electrical property of the sensing element is measured by the gas measuring device; and
   a control circuit having a heating element controller connected to, and measuring an electrical property of, the heating element, and the control circuit having a heater power supply supplying power to the heating element, wherein the heating element controller is connected to, and controls the operation of, the heater power supply using pulse modulation based on the measurement of the electrical property of the heating element, and wherein the heating element controller controls the heater power supply using a first set of power pulses having a first duration and using a second set of power pulses having a second duration that is different than the first duration to maintain the electrical property of the heating element at a substantially constant value.

2. The gas measuring device of claim 1, wherein the heating element is controlled to maintain a substantially constant temperature of the sensing element.

3. The gas measuring device of claim 1, wherein the heating element controller measures a resistance of the heating element, the heating element controller controlling the operation of the heater power supply based on the measured resistance of the heating element.

4. The gas measuring device of claim 1, wherein the sensor includes a substrate having the sensing element applied to one side of the substrate and the heating element applied to the opposite side of the substrate, the substrate thermally conducting heat from the heating element to the sensing element.

5. The gas measuring device of claim 1, wherein the control circuit further includes a sensing element controller connected to, and measuring the at least one electrical property of, the sensing element, the sensing element controller sharing computing resources with the heating element controller.

6. A gas measuring device for measuring a presence of a target gas in a fluid medium, the gas measuring device comprising:
   a sensor having a sensing element and a heating element being configured to heat the sensing element to a predetermined operating temperature, the sensing element being responsive to the target gas such that at least one electrical property of the sensing element varies based on a presence of the target gas;

a sensing circuit having a sensing power supply for supplying power to the sensing element and a sensing element controller measuring the at least one electrical property of the sensing element; and a heating circuit having a heater power supply supplying power to the heating element and a heating element controller connected to, and measuring at least one electrical property of, the heating element, wherein the heating element controller controls the operation of the heater power supply using pulse modulation based on the measurement of the electrical property of the heating element, and wherein the heating element controller varies the pulse modulation of the heater power supply using a first set of power pulses having a first duration and using a second set of power pulses having a second duration that is different than the first duration to maintain the electrical property of the heating element at a substantially constant value.

7. The gas measuring device of claim 6, wherein the heating circuit operates the heater power supply to maintain a substantially constant temperature of the heating element.

8. The gas measuring device of claim 6, wherein the heating circuit varies the pulse modulation of the heater power supply to maintain the sensing element at a predetermined operating temperature.

9. The gas measuring device of claim 6, wherein the heating element controller measures a resistance of the heating element and varies the pulse modulation of the heater power supply to maintain a substantially constant resistance at the heating element.

10. A method of manufacturing a gas measuring device comprising:

providing a sensor having a sensing element and a heating element being configured to heat the sensing element to a predetermined operating temperature, the sensing element being responsive to a target gas such that at least one electrical property of the sensing element varies based on a presence of the target gas;

connecting a sensing control circuit to the sensing element, wherein the sensing control circuit supplies power to the sensing element and measures changes in the at least one electrical property of the sensing element relating to the presence of the target gas; and connecting a heating control circuit to the heating element, wherein the heating control circuit supplies power pulses to the heating element according to a pulse modulated control scheme and measures at least one electrical property of the heating element, wherein the power pulses of the pulse modulated control scheme are varied using a first set of power pulses having a first duration and using a second set of power pulses having a second duration that is different than the first duration to maintain the measured electrical property of the heating element at a substantially constant value.

11. The method of claim 10, wherein the connecting a heating control circuit to the heating element includes connecting a heating control circuit to the heating element such that the heating control circuit measures an electrical property that varies based on temperature and the heating control circuit maintains a substantially constant temperature of the heating element by maintaining the measured electrical property at the substantially constant value by varying the pulse modulated control scheme.

12. A method of operating a gas measuring device comprising:

providing a sensor having a sensing element and a heating element being configured to heat the sensing element to a predetermined operating temperature;

supplying power to the heating element;

utilizing pulse modulation to control power to the heating element;

determining a resistance of the heating element;

utilizing a change in the resistance of the heating element to change the pulse modulation from a first set of power pulses having a first duration to a second set of power pulses having a second duration that is different than the first duration to maintain the heating element at a substantially constant temperature; and measuring a resistance of the sensing element, wherein the sensing element is responsive to a target gas such that the resistance of the sensing element varies based on a presence of the target gas.

13. The gas measuring device of claim 6, wherein the heating element controller maintains a substantially constant temperature of the heating element by maintaining the electrical property of the heating element at the substantially constant value.

14. The method of claim 12, wherein utilizing a change in the resistance of the heating element comprises comparing the determined resistance of the heating element to a desired operating resistance.

15. The gas measuring device of claim 1, wherein the electrical property of the heating element comprises a resistance of the heating element.

16. The gas measuring device of claim 1, wherein the heating element controller is configured to further vary at least one of an amount of voltage provided by the pulse modulation, a frequency of one or more pulses of the pulse modulation, or a shape of one or more pulses of the pulse modulation to maintain the electrical property of the heating element at the substantially constant value.

17. The gas measuring device of claim 6, wherein the heating element controller further varies the pulse modulation of the heater power supply by varying at least one of an amount of voltage provided by the pulse modulation, a frequency of one or more pulses of the pulse modulation, or a shape of one or more pulses of the pulse modulation.

18. The method of claim 10, wherein the pulse modulated control scheme is further varied by varying at least one of an amount of voltage provided by the pulse modulation, a frequency of one or more pulses of the pulse modulation, or a shape of one or more pulses of the pulse modulation.

19. The gas measuring device of claim 1, wherein the control circuit further comprises a pulse modulation driver connected to the heating element controller for generating the first and second sets of power pulses.

* * * * *